United States Patent [19]

Wechsler

[11] Patent Number: 4,964,297

[45] Date of Patent: Oct. 23, 1990

[54] VISCOSIMETER

[76] Inventor: Lawrence I. Wechsler, 1 Wooleys La., Great Neck, N.Y. 11023

[21] Appl. No.: 416,046

[22] Filed: Oct. 3, 1989

Related U.S. Application Data

[63] Continuation-in-part of Ser. No. 148,011, Jan. 25, 1988, Pat. No. 4,873,872.

[51] Int. Cl.$^5$ ............................................. G01N 11/12
[52] U.S. Cl. ......................................................... 73/57
[58] Field of Search ...................... 73/57, 861.71, 440, 73/448; 368/95

[56] References Cited

U.S. PATENT DOCUMENTS

| | | | |
|---|---|---|---|
| 1,427,922 | 9/1922 | Tiffany | 73/57 |
| 1,790,948 | 2/1931 | Rodgers | 73/57 |
| 2,431,378 | 11/1947 | Eitzen et al. | 73/57 |
| 2,714,927 | 8/1955 | Stern et al. | 368/95 |
| 4,517,830 | 5/1985 | Gunn et al. | 73/57 |

FOREIGN PATENT DOCUMENTS

| | | | |
|---|---|---|---|
| 107843 | 7/1967 | Denmark | 73/861.71 |
| 933172 | 9/1955 | Fed. Rep. of Germany | 73/57 |

OTHER PUBLICATIONS

Roger Gilmont, "A Falling-Ball Viscometer", Instruments and Control Systems, Sept. 1963.

*Primary Examiner*—Hezron E. Williams
*Assistant Examiner*—Joseph W. Roskos

[57] ABSTRACT

An improved falling float viscosimeter for measurement of over a wide range of viscosities. Use of a plurality of float members, at least one of which contains an aperture, enables the device to measure multiple ranges. Rate of descent of the floats may be easily correlated to the absolute viscosity of the fluid under test. The set of floats may be supplied as part of a complete viscosimeter or separately for extension of range of exisiting instruments.

4 Claims, 1 Drawing Sheet

U.S. Patent
Oct. 23, 1990
4,964,297
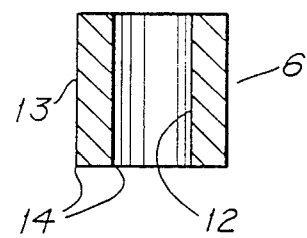
FIG. 1
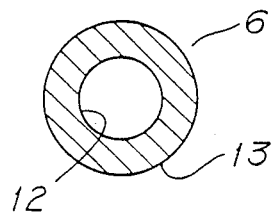
FIG. 2
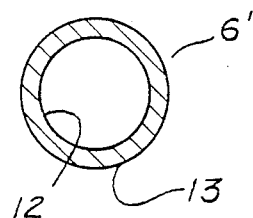
FIG. 3
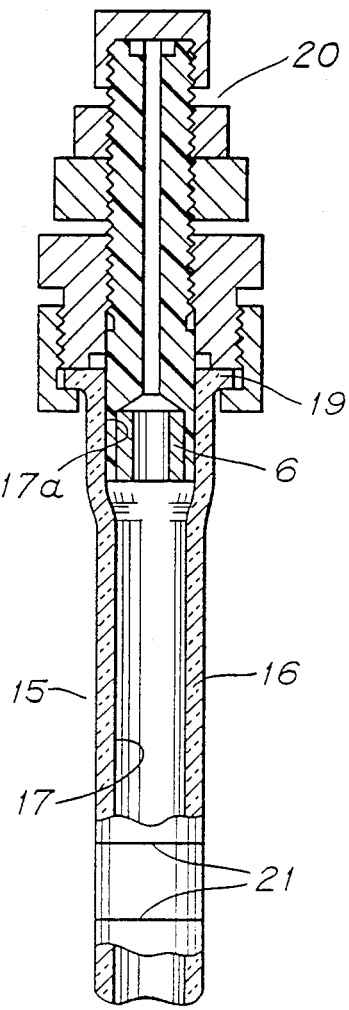
FIG. 4
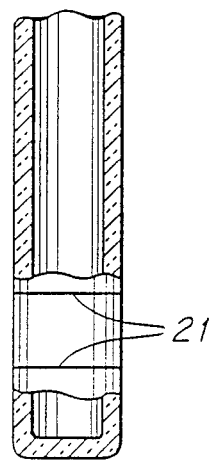

VISCOSIMETER

REFERENCE TO RELATED APPLICATION

This application is a Continuation-in-Part of my co-pending application Ser. No. 07/148,011 filed Jan. 25, 1988, now U.S. Pat. No. 4,873,872, entitled Float for Fluid Measurements.

BACKGROUND OF THE INVENTION

The present invention relates to viscosimeters and more particularly to such devices utilizing falling floats to measure the viscosity of fluids.

Viscosity measurement devices employing falling bodies which interact with the fluid under test are well known. Generally these consist of a transparent tube, closed at one end, and having a precision bore of constant internal diameter. The falling body, or float, having a diameter smaller than the inside diameter of said tube, describes an annular orifice of constant cross sectional area which is independent of the position of the float within the tube. At the open end of the tube the device may be equipped with a float release mechanism which is useful in holding the float in place until a measurement is to be taken. In order to take a reading, the tube is filled with a test fluid, the instrument is held in a vertical position, and the float is released and allowed to fall through the fluid. The float accelerates until it reaches a constant rate of speed, referred to as the terminal velocity. Time of descent is measured as it traverses a given distance, indicated by reference lines marked on the tube. From this information the viscosity of the fluid may be determined.

Since the rate of descent of the falling float is dependant on the shape as well as the size of the orifice formed between the tube and float, it is essential that the float remain centered during its descent. For this reason the outer tube is generally constructed with flats or beads, to insure concentricity. The use of such stabilizing flats may be avoided by maintaining only minimal clearance between the tube and the float, and by providing the float itself with an aperture through which the fluid may flow. Several devices employing such members are described in the prior art.

Gunn, deceased et al, U.S. Pat. No. 4,517,830 describes a viscosity measurement device in which blood viscosity may be determined immediately after withdrawal of the sample from the donor. The device consists of a hypodermic syringe in which a float member has been included such that the unit can operate as a falling float viscosimeter. The use of an apertured member is suggested in order to maintain concentricity during its descent. Although describing a float of similar structure to the present invention, Gunn does not suggest any means of extending the range of viscosities that the device is capable of measuring. Since the instrument is intended for the measurement of blood samples only, it is apparent that the float structure was selected solely to obviate the need for flats or beads on the inner surface of the syringe tube, which might otherwise interfere with the operation of the device. The Gunn device is not useful where values of viscosity vary widely and therefore no attempt was made to describe a generalized correlation between time of descent and absolute viscosity of the test fluid.

For applications requiring measurement of a range of viscosities rather than single values, it is desirable to have some means, whether experimental or theoretical, of correlating the absolute viscosity to the rate of descent of the falling body. In Heinz, German Patent No. 933172, a falling float viscosimeter is described in which the cylindrical float is provided with a capillary aperture. Minimal clearance is maintained between the float and the tube causing the fluid to flow only through the narrow, central aperture. Poisselle's equations, governing flow through capillaries, are used to determine the viscosity from the physical properties of the viscosimeter and the rate of descent of the float. This correlation however, only applies when the aperture is a capillary. The bore must also be sufficiently long such that entrance and exit effects would not introduce significant error. As a result, the range of viscosities that the device is capable of measuring is extremely limited.

A method of correlation more widely used for general viscometry work involves the determination of a viscosimeter constant. It has been shown that for a given viscosimeter, with a float and fluid of given densities, the viscosity of the fluid is directly proportional to the time of descent of the float falling at terminal velocity, provided measurement is limited to the Stokes region. The viscosimeter constant may be determined empirically, by measurement of a standard solution of known viscosity. It has also been suggested that the constant may be predicted theoretically from the dimensions of the tube and float. In the paper, A Falling-Ball Viscometer, by Roger Gilmont, Instruments and Control Systems, Sept. 1963, it was demonstrated that by applying equations governing flow through the annulus of a rotameter type flowmeter, the value of the viscosimeter constant could be expressed as a simple function of tube and float diameters, and the distance of travel at terminal velocity within the Stokes region. Application of flowmeter theory is justified, since there is essentially no difference between a float falling at constant velocity through stationary fluid, and fluid flowing past a stationary float.

In order for a viscosimeter to handle a wider range of viscosities it is most often necessary to alter the physical characteristics of either the float or the tube. Selecting a float material of greater density is one method by which range may be increased. However, where corrosive substances are to be measured, the choice of compatible float materials is limited Another alternative is to increase the viscosimeter constant by enlarging the orifice through which the fluid may travel. In the case of a solid float, such as a sphere, where flow is between the tube and float, this is accomplished by an increase in tube diameter, or by use of a smaller float. In either case an additional viscosimeter must be constructed, since a new tube is required.

In Eitzen et al, U.S. Pat. No. 2,431,378, a viscosimeter is described in which the falling body consists of a hollow cylindrical cup, open at the top, and having one or more apertures through which the displaced fluid may travel during measurement. Minimal clearance is maintained between the top lip of the cup and the outer tube to avoid wobbling. The cup-shaped structure serves to reduce the effective density of the float as compared with a solid float of comparable size, making the instrument especially desirable in applications requiring the measurement of fluids of extremely low viscosity. When designing a viscosimeter to measure fluids of higher viscosity, it is suggested that the float apertures may be enlarged to allow increased flow. However, because of the reduced effective density of the cup-like structure, a heavier cup is required to measure very viscous fluids. Although a new tube need not be constructed in order to measure the higher viscosity, correlation of absolute viscosity with time of descent is difficult. Due to the particular geometry of the float, enlargement of the apertures has little effect on the weight of the float, while the surface area perpendicular to flow is reduced. Both the effective density and the viscosimeter constant are affected as a result. The effect is the same when the weight of the float is increased to accommodate fluids of very high viscosity. This, combined with the complex structure of the float, makes the theoretical prediction of the factor relating viscosity with time of descent virtually impossible. No acceptable means of correlating rate of fall to viscosity are suggested in Eitzen, and since the device contains only a single float, it is incapable of measurement over a wide range. The complex nature of the float also makes manufacture costly, and limits the choice of materials from which it can be constructed.

Accordingly, the basic object of the present invention is to provide an improved viscosimeter of the falling float type, capable of continuous measurement over an extended range of viscosities.

Another object is to provide a viscosimeter in which the viscosity may be readily determined from time of the float's descent, without the need for frequent recalibration.

A further object is to provide these improved characteristics in a device which is accurate, reliable, corrosion resistant, and economical to produce.

SUMMARY OF THE INVENTION

The present invention is an improved viscosimeter which employs multiple floats for the accurate measurement of viscosity over a wider range than was previously possible. The device is intended to be used with a set of floats, each with a different size aperture, and each capable of measuring a particular range of viscosities. The unique shape of the floats allows continuous measurement over several ranges; each float covering a specified range without the need of a new outer tube. The viscosimeter constant for each float, relating viscosity to time of descent, may be easily and accurately determined.

The shape of the floats are generally cylindrical or frustrum shaped, but may be any suitable shape symmetric about a central axis. These are provided with a coaxial aperture or apertures such that the remaining float material is of uniform thickness. Thus, when a cylindrical float is used, the aperture is of uniform internal diameter. Similarly, when the float is frustrum shaped, the bore is tapered such that the inner wall is parallel with the outer wall. The larger the aperture, the greater the viscosity that may be measured. One of the floats of the set may contain no aperture, and would be used to measure the lowest range of viscosities. In this arrangement, however, the outer tube must be constructed such that there is sufficient clearance between the tube and the float to create an annular orifice through which the test fluid may flow during the float's descent. Flats or beads would also be provided on the interior wall of the tube to maintain concentricity. In the case where all floats were equipped with apertures, no such annular orifice need be provided since all displaced fluid could flow through the floats themselves and concentricity would be assured by a minimum of clearance between the tube and float.

Unlike viscosimeters described in the prior art, the present device does not require a heavier float in order to handle an increased range of viscosities. By selecting and installing a float with a larger aperture, fluids with a higher viscosity may be measured. There is no need for a new outer tube since all other float dimensions remain constant. High viscosity fluids may be measured using a float with a larger aperture notwithstanding the resultant decrease in float weight. In addition, as the aperture size is increased, the weight of the float decreases proportionally to the reduction in surface area of the float perpendicular to the direction of travel, simplifying theoretical determination of the viscosimeter constant for each float. Since the density and overall size of the float remain unchanged, the constant correlating viscosity with time of descent varies only as a function of aperture diameter, which may be easily determined. The simple structure of the float described herein enables manufacture within close tolerances, further assuring accurate and convenient correlation.

The floats employed by the present invention may be supplied as part of a complete viscosimeter or may be provided separately to extend the range of existing devices. In the latter case, a viscosimeter with a limited range may be adapted to enable measurement of viscosities many times greater without great expense or complicated correlation procedures.

BRIEF DESCRIPTION OF THE DRAWINGS

FIG. 1 is an axial cross sectional view of a typical float member of the set with a single central aperture;

FIG. 2 is a cross sectional end view of the float member shown in FIG. 1;

FIG. 3 is a cross sectional end view of another of the float members of the set with a larger central aperture for measurement of higher viscosities;

FIG. 4 is a fragmentary axial cross sectional view of a falling float type viscosimeter wherein the float member of FIG. 1 & 2 is shown held in place by the release mechanism prior to the taking of a measurement.

DETAILED DESCRIPTION OF THE PREFERRED EMBODIMENT

Referring now to the drawings, and in particular FIG. 1 and 2, therein illustrated is a typical, cylindrically shaped float member according to the present invention, generally designated 6. The float 6 is formed of glass or other suitable material, and is provided with a precision bore aperture 12. The outer wall 13 of the float 6 is precision ground to a precise uniform diameter. The ends of the float 6 are cut flat and provided with fine chamfers 14.

FIG. 3 is a cross-sectional end view of another float of the set intended for measurement of viscosities greater than range covered by the float 6 shown in FIG. 1 and 2. The float, generally designated 6', is formed from the same material and is the same overall length as the float 6 in FIG. 1 and 2, as are all other floats of the set. The diameter of the outer wall 13 is also identical for all members intended for use within a particular viscosimeter. The precision bore aperture 12' is larger in diameter than the aperture 12 shown in FIG. 1 and 2, providing the test fluid with increased cross-sectional area through which to flow, thereby allowing the measurement of greater viscosities. The decreased weight of the float due to enlargement of the aperture has no effect on its ability to measure the higher range.

It should be noted that the simple geometry of the float lends itself to the use of inexpensive production methods. Glass floats may be constructed by heat shrinking tubing of suitable dimensions around a precision ground mandrel, followed by centerless grinding of the float to insure accuracy of the outer diameter. Metallic floats could be fabricated from short lengths of rod through which a hole of precision bore is drilled.

Referring now to FIG. 4, therein illustrated is a falling float type viscosimeter which incorporates the float members according to the present invention, generally designated 15. The viscosimeter 15 comprises a tube 16 with a precision axial bore 17 of uniform diameter. The bore 17a is enlarged to a uniform inner diameter at one end, and the tube 16 is provided with an outward extending flange 19 at the same end. The tube 16 is sealed at the other end. Received within the tube is a float 6, cylindrically shaped and with an outside diameter 13 slightly smaller than the diameter of the bore 17.

Attached to the tube 16 by means of the flange 19 is a release mechanism 20. The release mechanism 20 may be adjusted such that the float 6 is held in place at the top of the tube 16. When a measurement is to be taken, the release mechanism 20 is re-adjusted and the float 6 is allowed to fall vertically within the tube 16. Reference lines 21 on the tube 16 indicate a distance of travel and by measurement of the time of descent of the float 6 falling freely through this given distance in a vertical position the viscosity of the fluid under test may be determined.

The present device is used with a set of two or more floats at least one of which is apertured. If a float containing no aperture is to be included in the set, additional clearance must be provided between the outer surface of the float and the inner wall of the tube. Stabilizing beads or flats running the length of interior of the tube may be added to insure concentric descent of the float.

Although only a few embodiments of the present invention have been disclosed herein in detail, various modifications thereon will become apparent to those skilled in the art. Accordingly, the spirit and scope of the invention are to be limited only by the appended claims.

I claim:

1. A viscosimeter comprising a straight tube which is closed at one end and has a uniform internal diameter and a plurality of members adapted to be disposed within the tube, at least one of the members having an aperture extending in the axial direction of the tube, and each apertured member having a thickness between the aperture and the periphery of the member which is uniform in the axial direction of the tube, the opening provided by the aperture in each of the apertured members being different for each of the members respectively, whereby all members of the plurality of members fall through a fluid disposed in the tube at different rates, thereby producing viscosity indications for different ranges of viscosity.

2. A viscosimeter comprising a straight tube which is closed at one end and has a uniform internal diameter and a plurality of members adapted to be disposed within the tube, each member having a cylindrical shape of uniform outside diameter extending in the axial direction of the tube, and at least one of the members having at least one aperture of uniform diameter extending in the axial direction of the tube, the total cross-sectional area of the apertures being different for each of the members respectively, whereby all members of the plurality of members fall through a fluid disposed in the tube at different rates, thereby providing viscosity indications for different ranges of viscosity.

3. A method for measuring viscosity of a fluid comprising; disposing the fluid into a straight tube which is closed at one end and has a uniform inside diameter; selecting a member from a plurality of members adapted to be disposed within the tube, at least one of the members having an aperture extending in the axial direction of the tube, and each apertured member having a thickness between the aperture and the periphery of the member which is uniform in the axial direction of the tube, the opening provided by the aperture in each apertured member being different for each of the members respectively, whereby all members of the plurality of members fall through a fluid disposed within the tube at different rates; and inserting the selected member into the tube and determining the rate at which the selected member falls through the fluid disposed in the tube, thereby producing viscosity indications for different ranges of viscosity.

4. A method for measuring viscosity of a fluid comprising; disposing the fluid into a straight tube which is closed at one end and has a uniform inside diameter; selecting a member from a plurality of members adapted to be disposed within the tube, each member having a cylindrical shape of uniform outside diameter extending in the axial direction of the tube, at least one of the members having at least one aperture extending in the axial direction of the tube, the total cross-sectional area of the apertures being different for each of the members respectively, whereby all members of the plurality of members fall through fluid disposed in the tube at different rates; and inserting the selected member into the tube and determining the rate at which the selected member falls through the fluid disposed in the tube, thereby producing viscosity indications for different ranges of viscosity.

* * * * *